United States Patent [19]
Tung et al.

[11] 4,205,016
[45] May 27, 1980

[54] MULTIFUNCTIONAL LITHIUM CONTAINING INITIATOR

[75] Inventors: Lu H. Tung; Grace Y-S. Lo; Joseph W. Rakshys; Douglas E. Beyer, all of Midland, Mich.

[73] Assignee: The Dow Chemical Company, Midland, Mich.

[21] Appl. No.: 931,790

[22] Filed: Aug. 7, 1978

Related U.S. Application Data

[60] Division of Ser. No. 859,356, Dec. 12, 1977, which is a continuation-in-part of Ser. No. 601,577, Aug. 1, 1975, abandoned.

[51] Int. Cl.$^2$ .................................... C07F 1/02
[52] U.S. Cl. .......................... 260/665 R; 260/439 CY; 568/635; 568/636; 568/641
[58] Field of Search ..... 260/665 R, 439 CY, 340.5 R; 568/635, 636, 641

[56] References Cited

U.S. PATENT DOCUMENTS

| | | |
|---|---|---|
| 3,509,188 | 4/1970 | Halasa et al. ................. 260/439 CY |
| 3,660,536 | 5/1972 | Ayans et al. ..................... 260/665 R |
| 3,663,585 | 5/1972 | Langer et al. ................. 260/439 CY |
| 3,663,634 | 5/1972 | Morton et al. .................... 260/665 R |
| 3,668,263 | 6/1972 | Morrison et al. ................. 260/665 R |
| 3,734,972 | 5/1973 | Naylor et al. ..................... 260/665 R |
| 3,734,973 | 5/1973 | Farrar .............................. 260/665 R |
| 3,776,964 | 12/1973 | Morrison et al. ................. 260/665 R |
| 3,784,637 | 1/1974 | Farrar .............................. 260/665 R |
| 3,787,510 | 1/1974 | Farrar .............................. 260/665 R |
| 3,848,008 | 11/1974 | Fetters ............................. 260/665 R |

*Primary Examiner*—Helen M. S. Sneed
*Attorney, Agent, or Firm*—R. B. Ingraham

[57] ABSTRACT

Highly desirable multifunctional lithium containing initiators are prepared by reacting a compound such as an organo lithium with an organic compound containing at least two 1,1-diphenylethylene groups. Such initiators can be prepared in the absence of polar solvents and are very desirable for the polymerization of dienes such as butadiene to a desirable 1,4 configuration. Several di-lithium compounds have been employed to initiate polymerization of various unsaturated organic monomers.

16 Claims, No Drawings

MULTIFUNCTIONAL LITHIUM CONTAINING INITIATOR

This is a division of application Ser. No. 859,356, filed Dec. 12, 1977, which is a continuation-in-part of application Ser. No. 601,577, filed Aug. 1, 1975, now abandoned.

In the polymerization of 1,3-butadiene and isoprene, for many applications, it is highly desirable to polymerize the monomer in such a manner that the amount of 1,4 addition in the polydiene chains is maximized. Desirable initiators of polymerization are often polyfunctional lithium compounds, that is, compounds having two or more lithium atoms as the polymerization initiating sites and are desirable in the preparation of block copolymers and diene polymers having functional end groups. Many of these multifunctional compunds, from a practical standpoint, fail to provide all that is desired in a polymerization initiator for vinyl group containing compounds such as 1,3-butadiene, isoprene and the like. Oftentimes, traces of polar compounds such as ethers are present. Polar compounds in general tend to increase the amount of 1,2 addition during the polymerization of butadiene or isoprene. Usually it is very desirable to polymerize the diene in a hydrocarbon solvent. For uniformity of the product and maximum control, as well as ease of handling, it is desirable that an initiator be soluble or readily made soluble in the polymerization system rather than merely dispersible as a particulate material. Multifunctional lithium containing initiators are well known in the art as is the use of such initiators in the polymerization of olefinically unsaturated hydrocarbon monomers. Such polymers and initiators are disclosed in the following U.S. Pat. Nos.: 3,660,536; 3,663,634; 3,668,263; 3,684,780; 3,725,368; 3,734,973; 3,776,893; 3,776,964; 3,784,637; 3,787,510; and 3,954,894, the teachings of which are herewith incorporated by reference thereto.

It would be desirable if there were available an improved multifunctional lithium containing compound suitable for initiation of polymerization in a hydrocarbon medium.

It would also be desirable if an initiator would be available which would promote polymerization of a 1,3-diene to give a high degree of 1,4 addition.

It would also be desirable if such an initiator were soluble or readily made soluble in polymerization initiation quantities in a hydrocarbon medium.

These benefits and other advantages in accordance with the present invention are achieved in a multifunctional, lithium containing, polymerization initiating compound of the Formula:

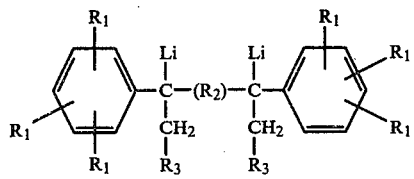

wherein $R_1$ is individually selected from the group consisting of hydrogen, an alkyl hydrocarbon radical, a cycloalkyl hydrocarbon radical, alkoxy radical, and an aromatic radical with the further limitation that $R_1$ contains from 0 to 16 carbon atoms. When $R_1$ is an alkyl radical, it is preferred that the alkyl radical has a tertiary carbon atom directly attached to the aromatic ring.

$R_2$ is a divalent organic radical having at least 6 carbon atoms, $R_2$ having at least one aromatic ring and an aromatic ring being directly attached to a carbon which is attached to a lithium atom, with the further limitation $R_2$ contains carbon and hydrocarbon, and optionally oxygen, iron, and/or sulfur. Oxygen and sulfur when present are present only in a configuration of a diphenyl oxide or diphenyl sulfide, iron in the ferrocene configuration; $R_2$ can be an aprotic organic solvent soluble oligomer or polymer. Preferably $R_2$ contains 6 to 12 carbon atoms and more preferably is 1,4-phenylene, 4,4'-biphenylene or 4,4'-oxybisphenylene.

$R_3$ is selected from the group consisting of alkyl, cycloalkyl, and aromatic radicals containing from 1 to 20 carbon atoms, and preferably secondary butyl.

Also contemplated within the scope of the present invention is a solution particularly suited for the initiation of polymerizing of vinyl group containing compounds which are polymerizable in the presence of a lithium containing catalyst, particularly vinyl hydrocarbon compounds, the solution comprising a major portion of a solvent selected from the group consisting of liquid aliphatic, cycloaliphatic and aromatic hydrocarbons and mixtures thereof and a minor proportion of a multifunctional lithium containing polymerization initiating compound of the Formula:

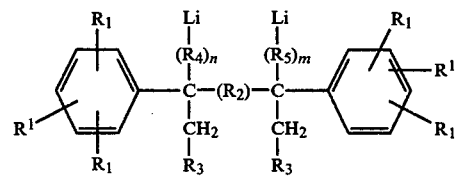

wherein $R_1$ is individually selected from the group consisting of hydrogen, an alkyl hydrocarbon radical, a cycloalkyl hydrocarbon radical, alkoxy radical, and an aromatic radical with the further limitation that $R_1$ contains from 0 to 16 carbon atoms. When $R_1$ is an alkyl radical, it is preferred that the alkyl radical has a tertiary carbon atom directly attached to the aromatic ring.

$R_2$ is a divalent organic radical having at least 6 carbon atoms, $R_2$ having at least one aromatic ring and an aromatic ring being directly attached to a carbon which is attached to a lithium atom, with the further limitation $R_2$ contains carbon and hydrocarbon, and optionally oxygen, iron, and/or sulfur. Oxygen and sulfur when present are present only in a configuration of a diphenyl oxide or diphenyl sulfide, iron in the ferrocene configuration; $R_2$ can be an aprotic organic solvent soluble oligomer or polymer. Preferably $R_2$ contains 6 to 12 carbon atoms and more preferably is 1,4-phenylene, 4,4'-biphenylene or 4,4'-oxybisphenylene.

$R_3$ is selected from the group consisting of alkyl, cycloalkyl, and aromatic radicals containing from 1 to 20 carbon atoms, and preferably secondary butyl.

$R_4$ and $R_5$ are individually selected from the group consisting of chemically combined units 1,3-butadiene and isoprene and mixtures thereof where n+m is at least 20.

Also contemplated within the scope of the present invention is a method for the polymerization of vinyl compounds containing at least one vinyl group and particularly vinyl hydrocarbon compounds which are polymerizable in the presence of a lithium containing catalyst, the steps of the method comprising providing a compound of the Formula:

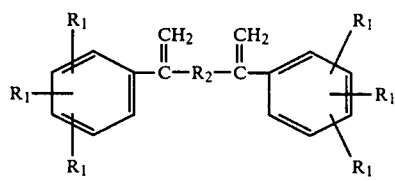

wherein $R_1$ is individually selected from the group consisting of hydrogen, an alkyl hydrocarbon radical, a cycloalkyl hydrocarbon radical, alkoxy radical, and an aromatic radical with the further limitation that $R_1$ contains from 0 to 16 carbon atoms. When $R_1$ is an alkyl radical, it is preferred that the alkyl radical has a tertiary carbon atom directly attached to the aromatic ring.

$R_2$ is a divalent organic radical having at least 6 carbon atoms, $R_2$ having at least one aromatic ring and an aromatic ring being directly attached to a carbon which is attached to a lithium atom, with the further limitation $R_2$ contains carbon and hydrocarbon, and optionally oxygen, iron, and/or sulfur. Oxygen and sulfur when present are present only in a configuration of a diphenyl oxide or diphenyl sulfide, iron in the ferrocene configuration; $R_2$ can be an aprotic organic solvent soluble oligomer or polymer. Preferably $R_2$ contains 6 to 12 carbon atoms and more preferably is 1,4-phenylene, 4,4'-biphenylene or 4,4'oxybisphenylene and mixtures thereof and a lithium containing compound of the Formula:

$R_3Li$ $R_3$ is selected from the group consisting of alkyl, cycloalkyl, and aromatic radicals containing from 1 to 20 carbon atoms, and preferably secondary butyl, adding to the hydrocarbon solution a member selected from the group consisting of butadiene, isoprene and mixtures thereof to provide a multifunctional compound having the Formula:

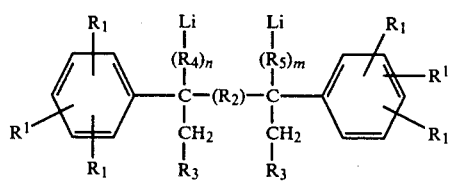

subsequently contacting the resultant dispersion with at least one lithium polymerizable monomer to cause the polymerization of the monomer to a corresponding polymer. $R_4$, $R_5$, n and m have the herein before described values.

Compounds employed herein include:

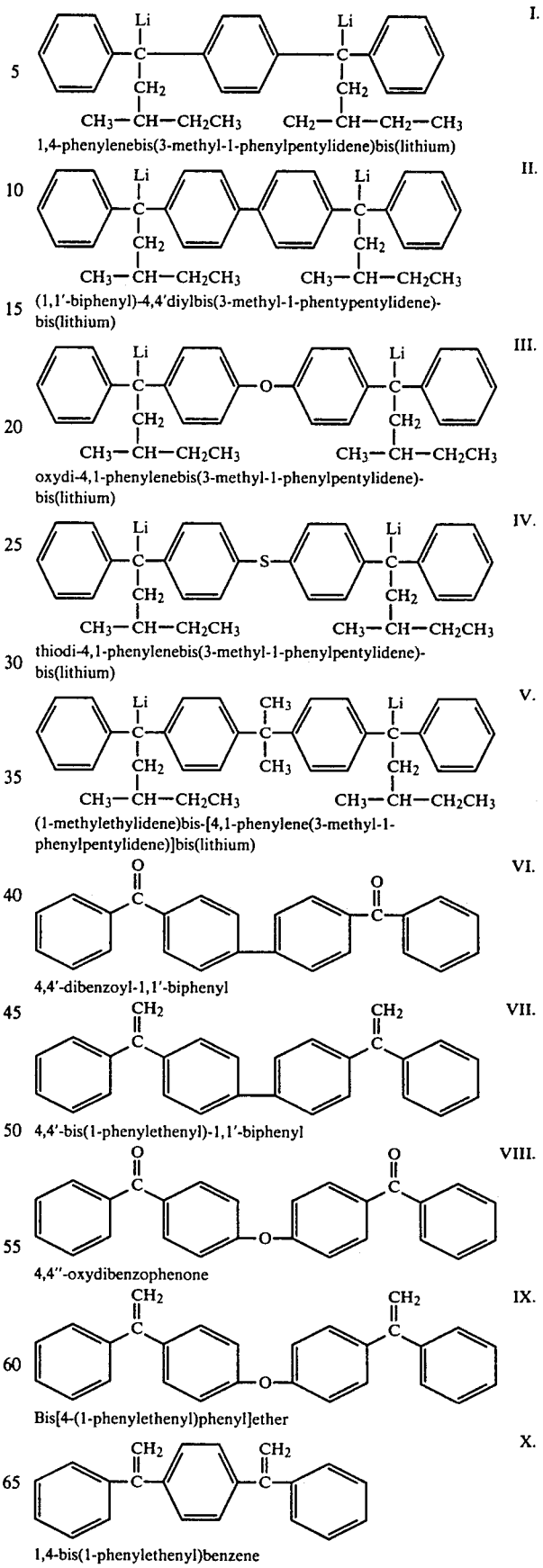

-continued

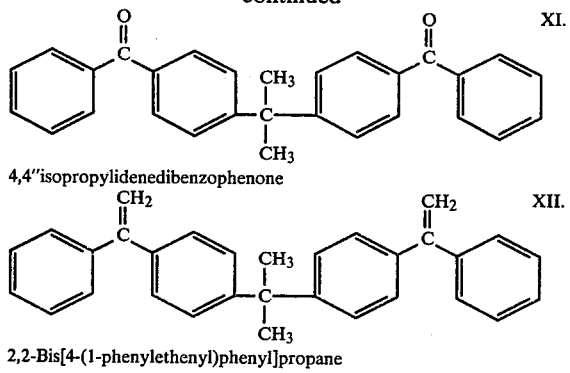

4,4″isopropylidenedibenzophenone 2,2-Bis[4-(1-phenylethenyl)phenyl]propane

Compounds in accordance with the present invention are readily prepared from compounds of the type hereinbefore disclosed and are readily synthesized by condensing an aromatic acid chloride with an aromatic compound such as benzene, biphenyl, diphenyl ether and the like in the presence of a Freidel-Crafts catalyst such as aluminum trichloride to form a diketone, the diketone having the ketone groups separated by at least one aromatic ring. The diketone compound is then subjected to a Wittig reaction which transforms the ketone groups into 1,1-vinylidene groups. The divinylidene compound is then contacted with an organic lithium compound such as secondary butyl lithium, tertiary butyl lithium and the like. The organo lithium compound adds to the double bond to provide the desired compound. The resulting dilithium compound on contact with small amount of butadiene or isoprene in an aliphatic, cycloaliphatic or aromatic hydrocarbon solvent such as hexane, cyclohexane or benzene becomes soluble. Generally the diene is employed in a proportion of from about 20 mole to about 200 mole per mole of the dilithium compound to render the compounds soluble.

EXAMPLE 1

A nitrogen purged reaction flask was charged with 23.4 grams of biphenyl dissolved in 50 milliliters of 1,2-dichloroethane. 85.5 grams of benzoylchloride and an additional 100 milliliters of 1,2-dichloroethane were added to the flask. The flask and contents were then cooled to about 10° C. and 71.5 grams of aluminum trichloride was added slowly to the mixture with stirring. The solution became dark red in color. Over a period of about four hours, the temperature of the reaction mixture was raised to 85° C. and maintained at that temperature for a period of 17 hours. At the end of 17 hours, the reaction mixture was poured into ice water with agitation. The reaction mixture and ice water were then extracted with about one liter of methylene chloride. The water layer was discarded and the methylene chloride containing the remaining mixture was washed with first, a sodium bicarbonate solution, and then with water. The methylene chloride solution was agitated with anhydrous sodium sulfate for 30 minutes, the mixture filtered and the filtrate evaporated to dryness. The crude product obtained on drying of the organic layer was then washed with methanol and subsequently with a 1 to 1 mixture of benzene and ethanol. The product was recrystallized from benzene.

17.6 grams of 4,4′-dibenzoyl-1,1′-biphenyl (Compound VI) were obtained having a melting range of 217°–218° C. Examination of the product with an infrared spectroscope indicated an absorbance of $>C=O$ which agreed with that of the absorbance of benzophenone.

Compound VI was converted to 4,4′-bis(1-phenylethenyl)-1,1′-biphenyl (Compound VII) in the following manner:

10.6 millimoles of n-butyllithium as a 0.53 Normal solution in benzene was admixed with 4.06 grams of methyltriphenylphosphonium bromide dissolved in 50 milliliters of tetrahydrofuran in a nitrogen-purged glass reaction vessel and the vessel maintained at ambient temperature (about 22° C.) for a period of 2 hours. A suspension of 2.05 grams of Compound VI in 30 milliliters of tetrahydrofuran was added to the reaction mixture. The reaction vessel was maintained at room temperature for a period of about 16 hours. At the end of this period, the tetrahydrofuran was evaporated and the remaining solid dissolved in a 1:1 by volume diethyl ether-water mixture. The ether and water were separated and the ether layer washed with water and subsequently the ether was evaporated. The crude product Compound VII was recrystallized twice from a 1 to 1 mixture of benzene and ethanol and the solid product obtained washed with n-hexane, the 4,4′-bis(1-phenylethenyl)-1,1′-biphenyl (Compound VII) had a melting point of 193°–196° C. A benzene solution of Compound VII was prepared in a nitrogen-filled serum bottle equipped with a magnetic stirrer. The solution contained 0.5 grams (1.41 millimoles) of Compound VII and 70 milliliters of dry benzene. 7.2 milliliters of 0.482 Normal secondary butyllithium n-hexane solution was injected into the serum bottle with a hypodermic syringe to provide 3.47 milliequivalents of sec-butyllithium. The mixture was stirred at room temperature for 2 hours and 40 minutes, and resulted in a deep blue colored dispersion.

The foregoing treatment of Compound VII was repeated and a 15 milliliter portion of the resulting dispersion was withdrawn and injected into a serum bottle containing nitrogen and 0.05 milliliter of glacial acetic acid. The dispersed material dissolved and the solution color turned from deep blue to yellow. Lithium acetate formed in the solution and was removed therefrom. An infrared spectrum of the remaining liquid showed a complete disappearance of the absorption band at 900 cm$^{-1}$ indicating that all vinyl groups had reacted with the sec-butyllithium. The deep blue dispersion obtained by the treatment of Compound VII resulted in the formation of Compound II. Butadiene was polymerized using Compound II in the following manner: A nitrogen purged reaction flask was charged with 850 milliliters of degassed dry benzene and the reaction mixture containing Compound II. About 10 grams of 1,3-butadiene monomer was added and the mixture agitated at room temperature for a period of about 1 hour and 35 minutes. During this period, the dispersion became a solution. An additional 40 grams of 1,3-butadiene were added and polymerization proceeded for about 40 minutes and the temperature of the reaction mixture was maintained at about 45°–55° C. The reaction mixture was subsequently cooled to room temperature and 4 milliliters of distilled tetrahydrofuran were added with agitation. When the tetrahydrofuran was uniformly dispersed, a solution of 2.44 milliequivalents of silicon tetrachloride in benzene was added. Visible gels formed immediately. After agitation for about 20 minutes, 1.5 milliliters of glacial acetic acid were added and the mixture containing the gel allowed to stand at room temperature overnight. The resultant polybutadiene contained 40 percent ungelled polymer and 60 percent gel, the foregoing being by weight thereby confirming that the initiator compound was difunctional. The theoretical gel content was 86 percent.

For purpose of comparison, the foregoing polymerization procedure was repeated with the exception that sec-butyllithium was employed as catalyst instead of Compound II. The recovered polybutadiene was completely soluble in tetrahydrofuran, toluene and benzene. No gels were observed.

EXAMPLE 2

Compound III was prepared in the following manner:
A nitrogen-purged reaction vessel was charged with 106.4 grams of aluminum trichloride and a solution of 91.94 grams of benzoylchloride dissolved in 200 milliliters of methylene chloride. The reaction vessel was cooled in an ice bath. A solution of 56 grams of diphenyloxide and 20 milliliters of methylene chloride was cooled to about 0° C. and added to the reaction vessel. After a period of two and one-half hours, the ice bath was removed and the vessel warmed to room temperature and held at ambient temperature for about 20 hours. After 20 hours, some of the methylene chloride had evaporated and was replenished. After an additional hour, the reaction mixture was poured over ice. The resultant aqueous mixture was extracted twice with methylene chloride. The water and organic layers were separated and the water layer was discarded. The organic layer was washed twice with a ten weight percent solution of potassium hydroxide in water. The water layer was discarded. The remaining organic layer was evaporated to dryness. The remaining crude product was dissolved in benzene and decolorized with charcoal. An equal volume of methanol was added to the decolorized benzene solution and 56.03 grams of 4,4''-oxydibenzophenone (Compound VIII), was obtained in the form of white, crystal platelets. The procedure of Example I was used to convert Compound VIII into bis[4-(1-phenylethenyl)-phenyl]ether (Compound IX). A nitrogen purged serum bottle was charged with 1.62 millimoles of Compound IX dissolved in 50 milliliters of dry benzene. Eight milliliters of a 0.482 Normal secondary butyllithium solution in hexane was added to the serum bottle by means of a syringe. A dark red dispersion of Compound III in benzene resulted. In a separate experiment the dispersion was acidified in the manner of Example I and an infrared spectral analysis indicated the absence of the 900 cm$^{-1}$ band indicating the absence of vinyl groups. A nitrogen purged reaction flask was charged with 780 milliliters of degassed dry benzene and the dispersion of Compound III containing 1.62 millimoles thereof and 10 grams of 1,3-butadiene. After about 90 minutes, the dispersion became a solution and an additional 60 grams of 1,3-butadiene was added. The butadiene polymerized over a period of about 1 hour and 2 milliliters of tetrahydrofuran were added with agitation. When the tetrahydrofuran had been uniformly dispersed, 2.09 milliequivalents of silicon tetrachloride in benzene were added. After about one hour, 1.3 milliliters of glacial acetic acid were added. Visible gels were formed when the silicon tetrachloride was added. The polybutadiene contained 56.6 percent gel. The theoretical amount of gel was calculated to be about 65 percent. The initiator was therefore difunctional. 1.18 millimoles of Compound IX was dissolved in 35 milliliters of dry benzene in a nitrogen-purged serum bottle. 2.46 milliequivalents of a hexane solution of secondary butyllithium was added to form the polymerization initiator Compound III. After a period of about two hours, the initiator mixture was added to a nitrogen purged reaction vessel containing 860 milliliters of degassed dry benzene. The vessel and contents were at ambient temperature about 23° C. About 10 grams of 1,3-butadiene were monomer were added. After a period of about 1 hour, a clear solution was obtained. Butadiene was then added to provide a total amount of about 88 grams. Polymerization proceeded to completion at temperatures between 45° and 55° C. The mixture was then cooled to room temperature and about 4 milliliters of distilled tetrahydrofuran were added. The reaction mixture was stirred for a period of about 15 minutes and 47 milliliters of styrene added. After the addition of the styrene, the vessel was maintained at room temperature overnight. The next morning, one and one-half milliliters of glacial acetic acid were added. The reaction mixture was a clear viscous mass. The polymer from the mass was recovered by precipitation by the addition of methanol. The resultant polymer was compression molded at about 190° C. The tensile strength at break of the polymer at ambient temperature was 1400 pounds per square inch when broken at a draw-rate of 20 inches per minute. The elongation of the specimen at break was about 700 percent. The molecular weight of the polymer as determined by Gel-Permeation Chromatography by the method described in the *J. Applied Polym. Sci.* 13, 2359 (1969) Runyon et al. was 325,000 total with a central block of polybutadiene of 221,000 and two styrene-end blocks of 52,000 each. The foregoing values being in molecular weight units.

An additional quantity of Compound III was prepared by charging to a nitrogen-purged flask 0.88 millimoles of Compound IX dissolved in 25 milliliters of dry benzene and adding thereto with agitating 1.85 milliequivalents of secondary butyllithium dissolved in 4.3 milliliters of hexane. Compound III began to form as a red dispersion in benzene. The dispersion was stirred for a period of 3½ hours at room temperature and 2 milliliters of isoprene were added to the dispersion. The dispersion was then heated to a temperature of about 60° C. and after a period of about 10 minutes the red dispersion changed to a reddish-brown solution. The solution was added to a nitrogen purged flask containing 40 grams of butadiene dissolved in 450 milliliters of dry benzene. The reaction mixture was maintained within the temperature range of 45° to 55° C. Polymerization of the butadiene was completed in about 50 minutes. The reaction mixture was then cooled to about 35° C. and 22 milliliters of styrene were added. The solution was stirred for about two minutes and 2 milliliters of distilled tetrahydrofuran were added. The temperature of the solution was maintained at about 35° C. for a period of about one hour, and 0.15 milliliters of glacial acetic acid added. The reaction mixture was diluted by the addition of methanol which caused precipitation of the polymer formed. The precipitate was separated from the liquid and vacuum dried at room temperature overnight. A portion of the polymer was compression molded in test bars at a temperature of about 180° C. The polymer had a tensile strength at break of 3245 lb. per square inch as measured at 23° C. and a jaw separation rate of 20 inches per minute. The elongation at break of the polymer sample was 1000 percent. The molecular weight of the polymer was determined by gel-permeation chromatography using the procedure herebefore referred to. The molecular weight was 123,000 with a central block of butadiene of 83,000 and two styrene-end blocks of 20,000 each.

EXAMPLE 3

A reaction flask was purged with nitrogen and charged with 58.5 grams of aluminum trichloride and 160 milliliters of benzene. A mixture of 40.6 grams of terephthaloyl chloride in 280 milliliters of benzene was added to the reaction flask from a dropping funnel over a period of 50 minutes. The temperature of the reaction mixture was maintained at about 44°-47° C. for a period of about 40 minutes and raised to 68° C. for about one and one-half hours. The reaction vessel and contents were cooled with ice water bath and ice water mixed with the reaction mixture. Methylene chloride was added and the aqueous and organic layers separated. The organic layer was washed three times with aqueous sodium bicarbonate and washed twice with water. The organic layer was dried over anhydrous sodium sulfate. The particulate sodium sulfate separated and the organic solvents removed by evaporation. The resultant crude product remaining after the evaporation was recrystallized from absolute alcohol containing about 0.5 percent benzene. Thirty grams of 1,4-dibenzoylbenzene were obtained which had a melting range of 155°-160° C. The 1,4-dibenzoylbenzene was then converted to 1,4-bis(1-phenylethenyl)benzene (Compound X), employing the procedure set forth in Example 1 wherein Compound VI was converted to Compound VII. A nitrogen-purged flask was charged with 0.98 millimoles of Compound X dissolved in 20 milliliters of dry benzene. Subsequently, 6 milliliters of 0.483 Normal sec-butyllithium-hexane solution was added. The mixture was stirred for 2 hours at room temperature. The mixture was a dark bluish red suspension and contains Compound I. A portion of the solution containing Compound I was acidified with glacial acetic acid and the infrared spectrum showed no peak in the 900 cm$^{-1}$ region which indicated the absence of a vinyl group. Butadiene was polymerized employing the dispersion containing Compound I. A nitrogen-purged reaction flask was charged with 450 milliliters of benzene and the dispersion containing Compound I. Ten grams of 1,3-butadiene was added to the flask. The flask and contents were maintained at a temperature of about 40° C. for about one-half hour, the dispersion became a solution and 28 grams of butadiene were added. The contents of the flask were warmed to about 45°-55° C. for a period of about 50 minutes. The reaction mixture and flask were then cooled to room temperature and 2 milliliters of distilled tetrahydrofuran were added with stirring. Subsequently, 1.12 milliequivalents of silicon tetrachloride in benzene were added. Gels were immediately obvious. After about 60 minutes, 0.1 milliliter of glacial acetic acid was added. The reaction mixture was stirred for 30 minutes. The following day, the product was recovered by precipitation by addition of methanol. The product contained 55 percent gel. The theoretical gel content was 67 percent therefore the initiator was difunctional.

EXAMPLE 4

Compound XI was prepared from 2,2-diphenylpropane and benzoylchloride using the same reaction conditions as set forth in Example I. The quantities of ingredients employed were: 2,2-diphenylpropane 20.8 grams, benzoylchloride 64.6 grams, aluminum trichloride 61 grams, and 1,2-dichloroethane 160 milliliters. The resultant diketone 4,4''-isopropylidenedibenzophenone (Compound XI) was obtained as a viscous brown high boiling oil and showed one main peak on a gas chromatogram. The infrared spectrum and the nuclear magnetic resonance spectrum both indicated that the product was the desired diketone (Compound XI). The above diketone (Compound XI) was subjected to the Wittig reaction employing conditions set forth in Example 1 for the conversion of the diketone to the corresponding diolefin compound to obtain 2,2-bis[4-(1-phenylethenyl)phenyl]propane (Compound XII). Compound XII was obtained as a dark brown viscous oil. The infrared spectrum and the nuclear magnetic resonance spectrum both indicated that Compound XII was obtained. Examination in a gas chromatograph indicated that the material had a purity of over 90 percent. A nitrogen-purged flask was charged with 2.15 millimoles of Compound XII dissolved in 20 milliliters of benzene. Twelve milliliters of 0.482 Normal sec-butyllithium in n-hexane was added. The reactants all were at room temperature. On addition of the sec-butyllithium solution, the color of the mixture changed to a reddish brown and suspended solids were slowly formed. The solution then contained Compound V. After the reaction mixture was agitated at room temperature for a period of 3 hours, it was employed as a polymerization initiator in the following manner: a nitrogen flushed reaction vessel was charged with 500 milliliters benzene, the dispersion containing Compound V and 10 grams of 1,3-butadiene. After a period of about one and one-half hours at which time 45 grams of butadiene were added, the mixture was maintained at a temperature of about 45°-50° C. and was cooled to room temperature after about 70 minutes. On cooling 6.5 milliliters of distilled tetrahydrofuran were added. On completion of the addition of tetrahydrofuran, and a short period of stirring 2.79 milliequivalents of silicon tetrachloride in benzene were added. On the addition of the silicon tetrachloride, gels became immediately obvious. The mixture was allowed to stand for about 20 minutes and 0.8 milliliters of glacial acetic acid was added and the mixture allowed to stand overnight. The following day, the polymer was recovered by precipitating with methanol and the resulting product found contained greater than 90 percent gel. Presence of gel indicated the difunctionality of the initiator.

EXAMPLE 5

A t-butystyrene-styrene-t-butylstyrene ABA triblock copolymer was prepared in the following manner:

A nitrogen filled one-liter flask was charged with 450 milliliters of degassed dry benzene and 55 milliliters of purified styrene. The resultant solution was titrated with a 0.56 N secondary butyllithium cyclohexane solution until a faint straw color appeared indicating removal or destruction of impurities which would react with the secondary butyllithium. Two milliliters of purified tetrahydrofuran and 0.394 millimoles of Compound III of Example 2 were added. The reaction mixture immediately turned a deep orange-brown color characteristic of the styryl anion. After 60 minutes the flask was cooled and an additional 30 minutes of standing at room temperature was allowed to insure that all of the styrene monomer was reacted. Purified tertiary butylstyrene, 2.9 milliliters, was then added to the flask which contained difunctional living polystyrene anions. Sixty minutes after the addition of the tertiary butylstyrene, one-half milliliter of glacial acetic acid was added to terminate the polymer. The polymer was precipitated, dried and weighed indicating about 100 percent conversion of monomer to polymer.

EXAMPLE 6

α,ω-dihydroxypolybutadiene was prepared in the following manner:

About two milliliters of liquid ethylene oxide was condensed in a fifty milliliter vial equipped with a high vacuum stopcock and a side arm, the side arm being capped with a rubber septum. To the condensed ethylene oxide was added four drops of 1.5 normal solution of normal butyllithium in hexane to inactivate any impurities which might be present in the ethylene oxide. The vial containing the treated ethylene oxide was then attached to a side arm of a one-liter reaction flask. The reaction flask was filled with nitrogen and about 450 milliliters of dry degassed benzene and about 25 grams of purified 1,4-butadiene. The residual impurities in the resultant mixture were inactivated by the addition of 0.42 milliequivalents of secondary butyllithium dissolved in cyclohexane. To the reaction mixture was added 0.56 millimoles of Compound III as prepared in Example 2. After the addition of Compound III, the mixture was heated to 55° C. and permitted to remain at this temperature for about 60 minutes. The mixture was maintained at this temperature by partial emersion of the flask in a water bath. At the end of 60 minutes, the water bath was removed and two milliliters of purified tetrahydrofuran added to the mixture. The viscosity of the reaction mixture lowered from the addition of the tetrahydrofuran. The contents of the vessel were continuously agitated and five minutes after the addition of the tetrahydrofuran, the stopcock of the vial containing the ethylene oxide was opened and the liquid ethylene oxide warmed by means of hot water to hasten the evaporation and transfer of the ethylene oxide as a gas into the reaction mixture. The viscosity of the reaction mixture increased rapidly and the straw yellow color of the butadienyl dianions disappeared almost completely after a period of about four minutes. The reaction mixture became a gel and agitation was stopped. The gel was allowed to stand for fifteen minutes and a one-milliliter portion of galical acetic acid was added and the gel structure disappeared. The acidified polymer was α,ω-dihydroxy polybutadiene.

When one employs the procedure of Example 1 wherein benzoyl chloride is replaced with paratoluic acid chloride, the following compound is obtained:

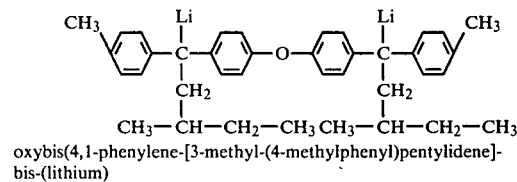
oxybis(4,1-phenylene-[3-methyl-(4-methylphenyl)pentylidene]-bis-(lithium)

The compound will have properties generally commensurate with the compound prepared in Example 1.

When the procedure of Example 1 is repeated wherein the benzoyl chloride is replaced with tertiarybutylbenzoyl chloride, the following compound is obtained:

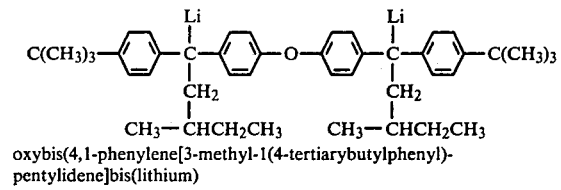
oxybis(4,1-phenylene[3-methyl-1(4-tertiarybutylphenyl)pentylidene]bis(lithium)

The compound will have properties generally commensurate with the compound prepared in Example 1.

When the procedure of Example 1 is repeated employing paraethylbenzoyl chloride, the following compound is obtained:

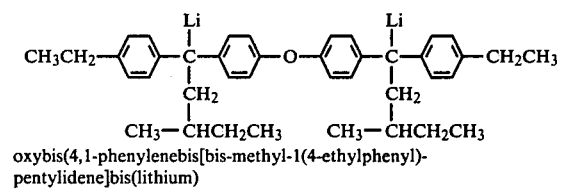
oxybis(4,1-phenylenebis[bis-methyl-1(4-ethylphenyl)pentylidene]bis(lithium)

The compound will have properties generally commensurate with the compound prepared in Example 1.

When the procedure of Example 1 is repeated employing 4-cyclohexylbenzoyl chloride, the following compound is obtained:

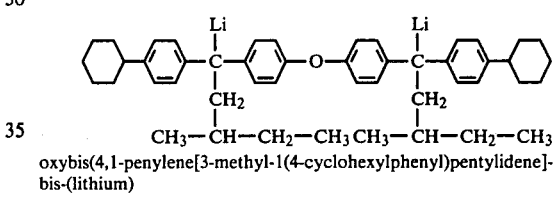
oxybis(4,1-penylene[3-methyl-1(4-cyclohexylphenyl)pentylidene]-bis-(lithium)

The compound will have properties generally commensurate with the compound prepared in Example 1.

When the procedure of Example 1 is repeated employing 3,4-dimethylbenzoyl chloride, the following compound is obtained:

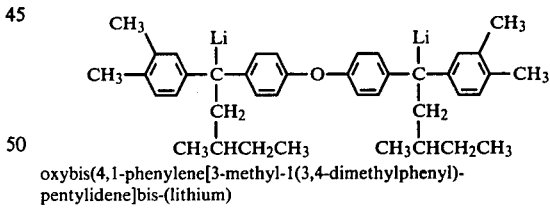
oxybis(4,1-phenylene[3-methyl-1(3,4-dimethylphenyl)pentylidene]bis-(lithium)

The compound will have properties generally commensurate with the compound prepared in Example 1.

When the procedure of Example 1 is repeated employing 4-phenylbenzoyl chloride in place of benzoyl chloride, the following compound is obtained:

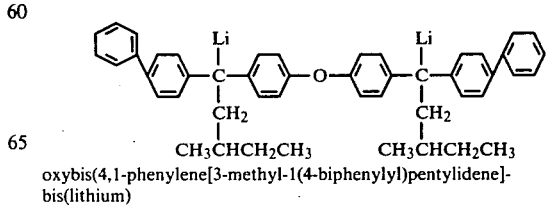
oxybis(4,1-phenylene[3-methyl-1(4-biphenylyl)pentylidene]-bis(lithium)

The compound will have properties generally commensurate with the compound prepared in Example 1.

When the procedure of Example 1 is repeated with the exception that 2-naphthoic acid chloride is employed in place of benzoyl chloride, the following compound is obtained:

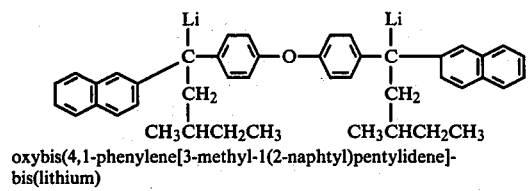
oxybis(4,1-phenylene[3-methyl-1(2-naphtyl)pentylidene]-bis(lithium)

The compound will have properties generally commensurate with the compound prepared in Example 1.

When the procedure of Example 1 is repeated with the exception that 4-phenoxybenzoyl chloride is employed in place of benzoyl chloride, the following compound is obtained:

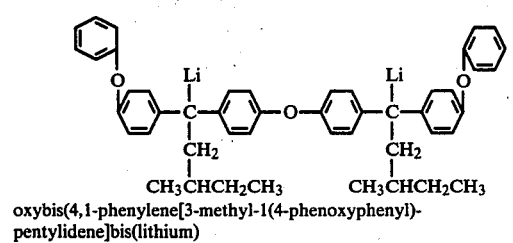
oxybis(4,1-phenylene[3-methyl-1(4-phenoxyphenyl)-pentylidene]bis(lithium)

The compound will have properties generally commensurate with the compound prepared in Example 1.

When the procedure of Example 1 is repeated with the exception that 4-methoxybenzoyl chloride is employed in place of benzoyl chloride, the following compound is obtained:

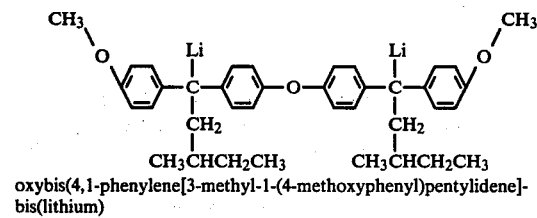
oxybis(4,1-phenylene[3-methyl-1-(4-methoxyphenyl)pentylidene]-bis(lithium)

The compound will have properties generally commensurate with the compound prepared in Example 1.

When the procedure of Example 1 is repeated with the exception that naphthalene is employed in place of diphenyl oxide, the following compound is obtained:

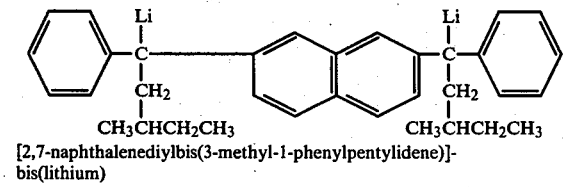
[2,7-naphthalenediylbis(3-methyl-1-phenylpentylidene)]-bis(lithium)

The compound will have properties, gnerally commensurate with the compound prepared in Example 1.

When the procedure of Example 1 is repeated with the exception that 1,4-diphenoxybenzene is employed in place of diphenyl ether, the following compound is obtained:

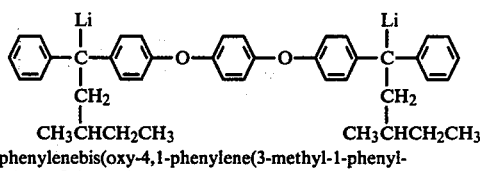
[1,4-phenylenebis(oxy-4,1-phenylene(3-methyl-1-phenyl-pentylidene)]bis-(lithium)

The compound will have properties generally commensurate with the compound prepared in Example 1.

When the procedure of Example 1 is repeated with the exception that 1,2-diphenoxy ethane is employed in place of diphenyl oxide, the following compound is obtained:

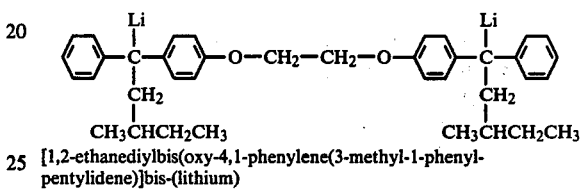
[1,2-ethanediylbis(oxy-4,1-phenylene(3-methyl-1-phenyl-pentylidene)]bis-(lithium)

The compound will have properties generally commensurate with the compound prepared in Example 1.

When the procedure of Example 1 is repeated with the exception that dibenzofuran is employed in place of diphenyl oxide, the following compound is obtained:

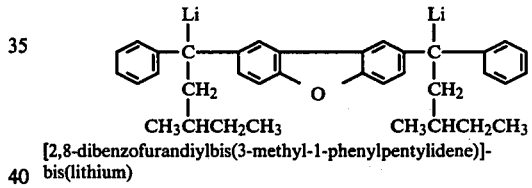
[2,8-dibenzofurandiylbis(3-methyl-1-phenylpentylidene)]-bis(lithium)

The compound will have properties generally commensurate with the compound prepared in Example 1.

When the procedure of Example 1 is repeated with the exception that 1,4-bis-2-phenylisopropylidene benzene was employed in place of diphenyl oxide, the following compound is obtained:

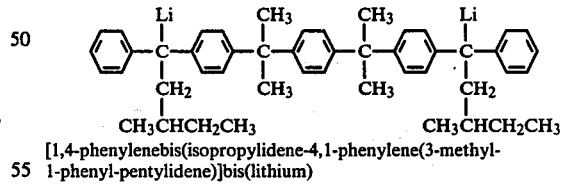
[1,4-phenylenebis(isopropylidene-4,1-phenylene(3-methyl-1-phenyl-pentylidene)]bis(lithium)

The Compound will have properties generally commensurate with the compound prepared in Example 1.

When the procedure of Example 1 is repeated with the exception that ferrocene is employed in place of diphenyl oxide, the following compound is obtained:

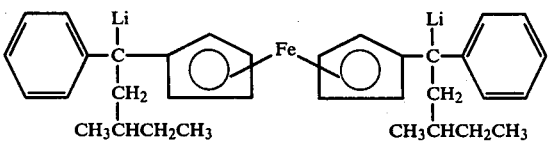

-continued

[ferrocene-1,1'-diylbis(3-methyl-1-phenylpentylidene)]-bis(lithium)

The compound will have properties generally commensurate with the compound prepared in Example 1.

When the procedure of Example 1 is repeated with the exception that normal butyl lithium is employed in place of secondary butyl lithium, the following compound is obtained:

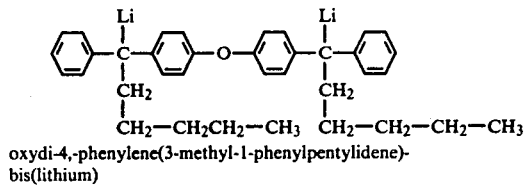

oxydi-4,-phenylene(3-methyl-1-phenylpentylidene)-bis(lithium)

The compound will have properties generally commensurate with the compound prepared in Example 1.

When the procedure of Example 1 is repeated with the exception that isopropyl lithium is employed in place of secondary butyl lithium, the following compound is obtained:

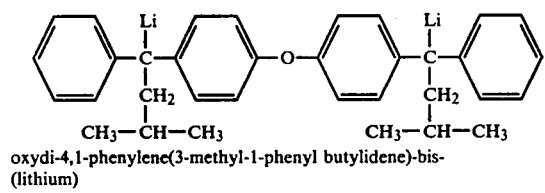

oxydi-4,1-phenylene(3-methyl-1-phenyl butylidene)-bis-(lithium)

The compound will have properties generally commensurate with the compound prepared in Example 1.

When the procedure of Example 1 is repeated with the exception that normal propyl lithium is employed in place of secondary butyl lithium, the following compound is obtained:

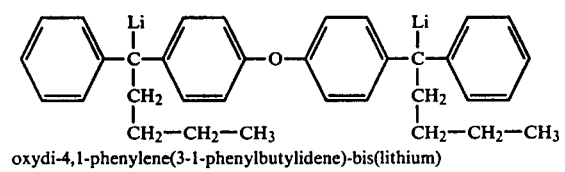

oxydi-4,1-phenylene(3-1-phenylbutylidene)-bis(lithium)

The compound will have properties generally commensurate with the compound prepared in Example 1.

In a manner similar to the foregoing illustrations, other dilithium initiators within the scope of the generic formula are readily prepared in the foregoing manner employing conditions substantially as hereinbefore set forth.

Initiators in accordance with the present invention are readily prepared in situ by maintaining a supply of the corresponding divinylidene compound. The divinylidene compound is readily and quickly converted to the corresponding lithium compound and solubilized by the addition of small quantities of monomer such as butadiene. If desired, the entire system can avoid the addition of polar compounds such as ethers, amines and the like and thus when employed the polymerization of diene polymers 1,2 addition is minimized; however, if it is desired, appropriate polar compounds may be added to increase 1,2 addition.

As the difunctional lithium initiators of the present invention provide a convenient means for the preparation of difunctional living polymers, such polymers are readily capped or terminated in conventional manner such as by the addition of carbon dioxide and subsequently hydrolysis to provide carboxyl group termination of the polymer molecules. Similarly, termination with dimethyl amino benzaldehyde results in a hydroxy dimethyl analine termination. The use of sulfuryl chloride and hydrolysis results in sulfonic acid groups. Glycidyl aldehyde can be employed to obtain hydroxy termination. The use of elemental sulfur results in termination in a mercaptan. Cyanogen chloride provides nitrile termination. Acidyl chloride provides ketone groups at each end of the polymer molecule and 2,4-toluene diisocyanate will provide an isocyanate termination; such capping or terminating reactions being well known in the art.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A multifunctional, lithium containing, polymerization initiating compound of the Formula:

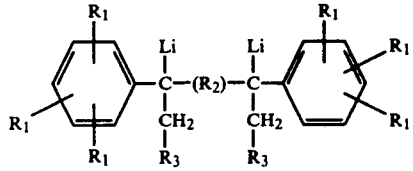

wherein
$R_1$ is individually selected from the group consisting of hydrogen, an alkyl hydrocarbon radical, a cycloalkyl hydrocarbon radical, alkoxy radical, and an aromatic radical with the further limitation that $R_1$ contains from 0 to 16 carbon atoms;
$R_2$ is a divalent organic radical having at least 6 carbon atoms, $R_2$ having at least one aromatic ring and the aromatic ring being directly attached to a carbon which is attached to an aromatic ring of the above formula, with the further limitation $R_2$ contains carbon and hydrocarbon, and optionally oxygen; oxygen when present is present only in the configuration of a diphenyl oxide;
$R_3$ is selected from the group consisting of alkyl, cycloalkyl, and aromatic radicals containing from 1 to 20 carbon atoms.

2. The compound of claim 1 wherein $R_2$ contains from 6 to 12 carbon atoms.

3. The compound of claim 2 wherein $R_2$ is a 1,4-phenylene radical.

4. The compound of claim 2 wherein $R_2$ is a 4,4'-biphenylene radical.

5. The compound of claim 2 wherein $R_2$ is a 4,4'-oxybisphenylene radical.

6. The compound of claim 1 wherein $R_3$ is a secondary butyl radical.

7. A multifunctional, lithium containing, polymerization initiating compound of the Formula:

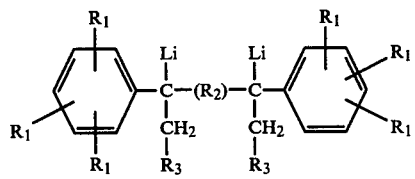

wherein
- $R_1$ is individually selected from the group consisting of hydrogen, an alkyl hydrocarbon radical, a cycloalkyl hydrocarbon radical, alkoxy radical, and an aromatic radical with the further limitation that $R_1$ contains from 0 to 16 atoms;
- $R_2$ is a divalent organic radical having at least 6 carbon atoms, $R_2$ having at least one aromatic ring, the aromatic ring being directly attached to a carbon which is attached to a lithium atom of the above formula, with the further limitation $R_2$ contains carbon and hydrocarbon, and optionally oxygen, iron, and/or sulfur, oxygen and sulfur when present are present only in the configuration of a diphenyl oxide or diphenyl sulfide, iron in the ferrocene configuration;
- $R_3$ is selected from the group consisting of alkyl, cycloalkyl, and aromatic radicals containing from 1 to 20 carbon atoms.

8. The compound of claim 7 wherein $R_2$ contains from 6 to 12 carbon atoms.

9. The compound of claim 8 wherein $R_2$ is a 1,4-phenylene radical.

10. The compound of claim 8 wherein $R_2$ is a 4,4'-biphenylene radical.

11. The compound of claim 8 wherein $R_2$ is a 4,4'-oxybisphenylene radical.

12. The compound of claim 7 wherein $R_3$ is a secondary butyl radical.

13. 1,4-phenylenebis(3-methyl-1-phenylpentylidene)bis(lithium).

14. (1,1'-biphenyl)-4,4'diylbis(3-methyl-1-phenylpentylidene)bis(lithium).

15. Oxydi-4,1-phenylenebis(3-methyl-1-phenylpentylidene)bis(lithium).

16. (1-methylethylidene)bis-[4,1-phenylene(3-methyl-1-phenylpentylidene)]bis(lithium).

* * * * *